United States Patent [19]

Hanley

[11] 4,232,215
[45] Nov. 4, 1980

[54] HUMAN REPRODUCTION INDEXING DEVICE

[76] Inventor: John P. Hanley, 625 Ivy Ct., Kenilworth, Ill. 60043

[21] Appl. No.: 947,568

[22] Filed: Oct. 2, 1978

[51] Int. Cl.³ .................... G06C 3/00; G06C 27/00
[52] U.S. Cl. ........................ 235/78 RC; 235/85 FC; 235/88 RC
[58] Field of Search ........ 235/85 FC, 78 RC, 88 RC, 235/88 R, 78 R

[56] References Cited

U.S. PATENT DOCUMENTS

| | | | |
|---|---|---|---|
| 2,638,272 | 5/1953 | Heck | 235/88 RC |
| 2,660,375 | 11/1953 | Carquillot | 235/88 R |
| 2,727,686 | 12/1955 | Thalmann | 235/85 FC |
| 3,215,344 | 11/1965 | Joffe | 235/88 RC |
| 3,468,037 | 9/1969 | Warneke | 235/88 R |
| 3,771,716 | 11/1973 | Sanchez | 235/85 FC |
| 4,035,616 | 7/1977 | Piringer | 235/78 RC |

Primary Examiner—L. T. Hix
Assistant Examiner—Benjamin R. Fuller
Attorney, Agent, or Firm—Emrich, Root, Lee, Brown & Hill

[57] ABSTRACT

A human reproduction indexing device for indicating the calendar dates for days of a menstrual cycle on which the probability of conception is the greatest includes a generally circular base member having indicia representing the calendar dates for the days of a given month disposed around the periphery thereof, and an index member rotatably secured to the base member and having an index and an indicator disposed thereon and configured so that when the index is aligned with the calendar date corresponding to the day of the onset of the menses, the indicator is positioned to indicate the calendar dates for a seven day interval starting ten days after the indexed date thereby indicating the time interval during which ovulation should occur and thus the days on which the probability of conception are the greatest.

16 Claims, 9 Drawing Figures

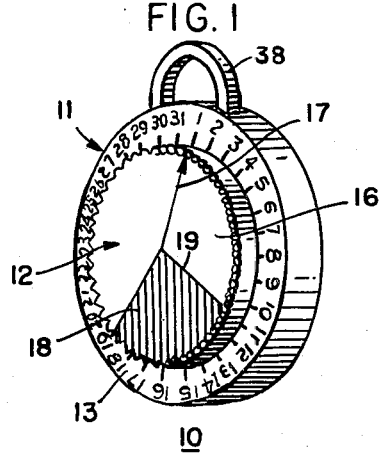
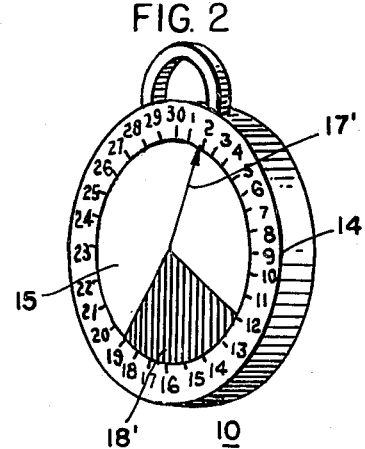
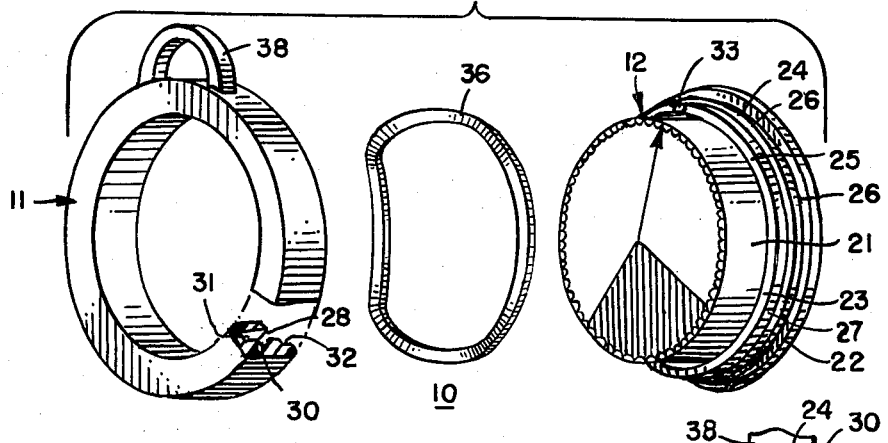
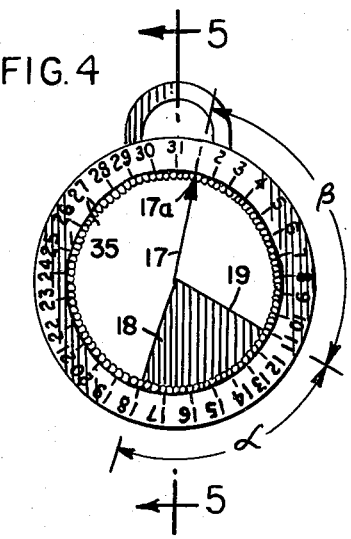
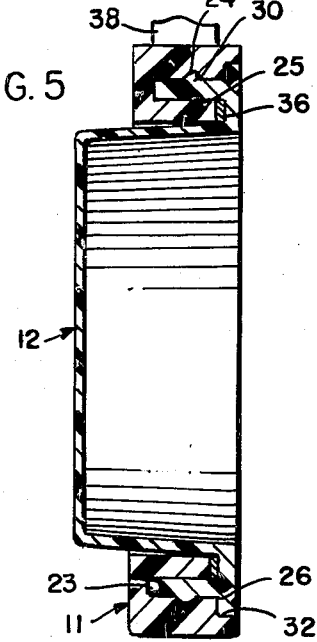

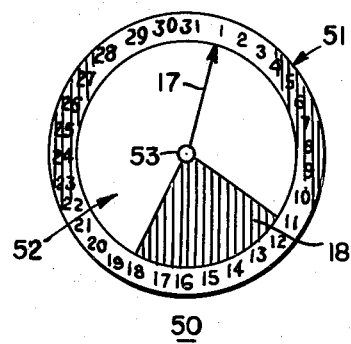
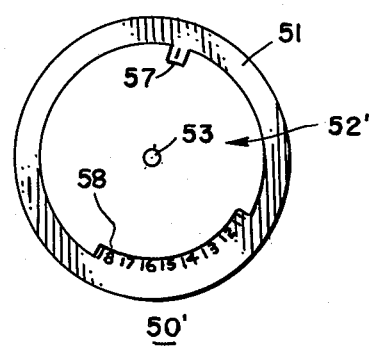
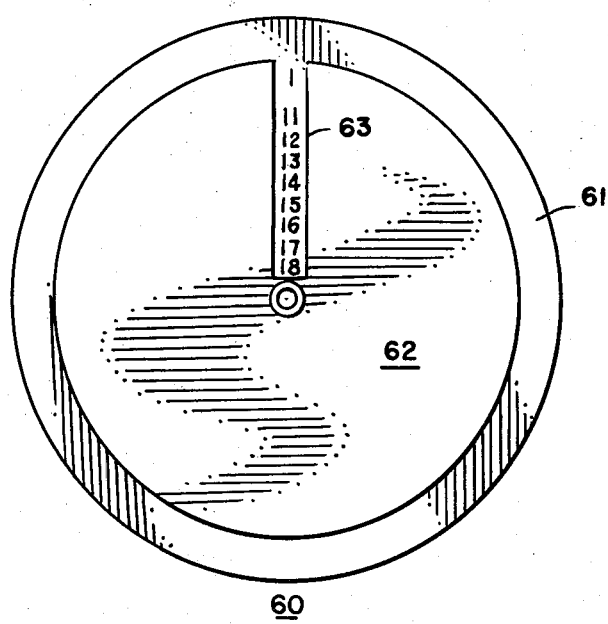
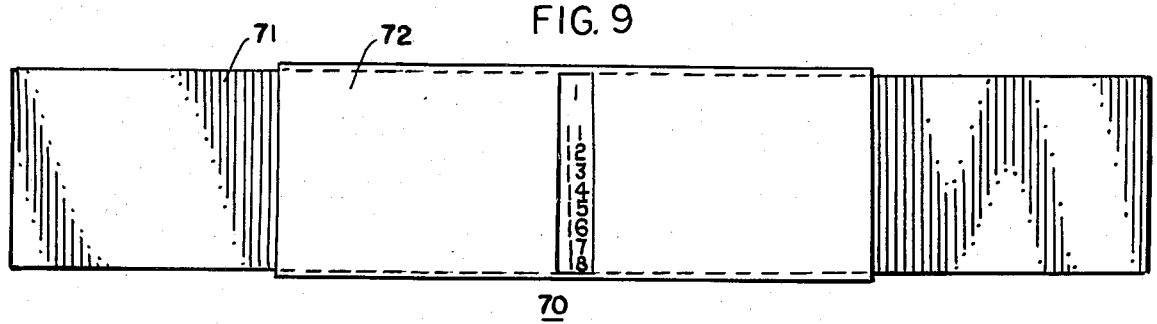

HUMAN REPRODUCTION INDEXING DEVICE

BACKGROUND OF THE INVENTION

1. Field of the Invention

This invention relates to a human reproduction indexing device for indicating the calender dates for days of a menstrual cycle on which the probability of conception is the greatest.

2. Description of the Prior Art

Timing is a very important consideration for those couples who want to have a baby as well as those who wish to practice some method of birth control. In particular, they must know the days of a menstrual cycle on which the probability of conception is the greatest. While it is generally known that there are a limited number of days during each month on which a woman can become pregnant, i.e. one to two days following ovulation, couples are often imprecise in guessing the fertile time because of misunderstandings as to the time of occurrance of ovulation, and how to predict when ovulation should occur.

There are a number of indirect methods for determining the time of ovulation. The method most frequently employed is the Basal body temperature (BBT) method which is based upon detection of the rise of a woman's body temperature that occurs around, or soon after the time of ovulation. However, the need to take and record daily temperatures is an inconvenience, and if it is not done the method loses its effectiveness. That is, the success of this method is dependent upon obtaining temperature readings regularly and upon proper interpretation of the recorded temperature information. Another method used by many females is the rhythm method. Although the rhythm method is one of the less effective methods of birth control, many females use this method because it conforms with their values. However, in many cases there are misunderstandings as to how the rhythm method is synchronized with the menstrual cycle, and this leads to misconceptions such as the ones that the highest risk of conception occurs just before and after menstruation.

In recent years, scientific approaches have been used to develop a way for predicting the woman's fertile period and the risk of conception. For example, an article by John C. Barrett and John C. Marshall entitled "The Risk of Conception on Different Days of the Menstrual Cycle" which appeared in *Population Studies*, Volume XXIII, No. 3, November, 1969, reports the results of a statistical analysis of data using a computer to correlate time of ovulation, frequency of coitus and the number of conception cycles. A mathematical function was developed which yielded the probability of conception on different days of the menstrual cycle. The study indicated that the risk of conception is small in the early part of the menstrual cycle. It increases noticeably about five days before ovulation and is maximum on the second day before ovulation. The risk of conception falls sharply by the second day following ovulation. The results of this study make it possible to predict high risk of conception times relative to ovulation. However, application requires use of the BBT method for the detection of the onset of ovulation.

A fertility indicator which obviates the need for using the BBT method has been developed for individual use by Reproduction Research Laboratories, Inc., Westport, Conn. The fertility indicator, which is a hand-held analog calculator, performs calculations of six variables affecting the optimal timing of sexual relations for conception. Although the device replaces basal temperature charts, which some couples find anxiety producing, the device is relatively expensive, and it would appear that medical counselling would be required to assure that the apparatus is used properly.

SUMMARY OF THE INVENTION

The present invention provides a human reproduction indexing device for indicating the calendar dates for days of a woman's menstrual cycle on which the probability of conception is the greatest. The indexing device comprises a base member bearing indicia representing the calendar dates for the days of a one month interval, and an index member movably secured to the base member and bearing indexing indicia including an index and an indicator configured such that when the index is aligned with the calendar date corresponding to the start of the menses, the indicator is located to indicate the calendar dates for a seven day interval, starting ten days after the indexed date. The midpoint of the seven day interval, which is approximately fourteen days after the start of the menses, closely corresponds to the time ovulation should occur for a woman having a typical twenty-eight day menstrual cycle. The three days on either side of the midpoint provides a guard against irregularity should ovulation occur earlier or later than expected and the life expectancy of the ova and the sperm.

In a preferred embodiment, the base member of the indexing device comprises an annular ring shaped element having the calendar date indicia disposed on the top surface thereof with the numbers representing the calendar dates for a month being equally spaced around the peripheral edge of such surface. The index member comprises a generally cylindrical element secured to the base member by way of a tongue and groove arrangement which interlocks the two members while permitting rotational movement of the index member relative to the base member.

The index member has a cylindrical main body portion which extends through the axial opening of the base member with the indexing indicia being disposed on the top surface of the main body portion. The index is in the shape of an arrow and the indicator is in the shape of an "arcuate" segment the angular width of which is selected so that the segment indicates seven dates of the calendar indicia on the base member. The arrowhead is located a preselected number of angular degrees from an edge of the indicator segment so that when the indexing device is set with the arrow aligned with the calendar date corresponding to the start of the menses, the indicator segment is located to indicate the calendar dates for the tenth through seventeenth days following the indexed date, thereby indicating a set of days including the day on which ovulation should occur. The indicator segment may be of a distinctive color, such as red. A bias spring interposed between the base member and the index member prevents inadvertant movement of the index member relative to the base member so that once the indexing device is set with the arrow indexed to a given date, the device remains set unless deliberately adjusted.

In another embodiment, the base member and the index member each comprise flat disc-shaped elements rotatably secured together by a rivet and having the same calendar date and indexing indicia as described above. A further embodiment employs an index member of approximately the same diameter as the base member with its edge overlying the calendar date indicia on the base member, the index member having cut out portions which expose the calendar dates. In a further embodiment, the calendar date indicia is duplicated in sets of seven days, with different sets corresponding to each of the thirty-one calendar days of the month scale. The sets of calendar days are selectively exposed through a radially extending slot provided in the index member. Moreover, a linear scale may be used with the index member having the configuration of a rectangular envelope with the base member extending therethrough. Slots in the index member expose the calendar dates for the days of the month and the corresponding set of seven calendar dates representing the days on which the probability of conception is the greatest. In all of the embodiments, the indexing device is preferably provided with calendar dates for a 31 day.

The indexing device is easy to use and provides an indication which is easily interpreted by the user. That is, once the index is set, the device clearly indicates the calendar dates for the days of a given menstural cycle on which there is the highest probability of conception and conversely the greatest risk of pregnancy.

DESCRIPTION OF THE DRAWINGS

FIG. 1 is a perspective view of a human reproduction indexing device provided in the present invention;

FIG. 2 is a perspective view showing the back side of the device shown in FIG. 1;

FIG. 3 is an exploded view of the indexing device shown in FIG. 1;

FIG. 4 is a front view of the indexing device of FIG. 1;

FIG. 5 is a sectional view taken along lines 5—5 of FIG. 4;

FIG. 6 is a plan view of a human reproduction indexing device provided in accordance with another embodiment of the invention.

FIGS. 7 and 8 show alternative arrangements for the indexing device shown in FIG. 6; and, FIG. 9 is a plan view of a human reproduction indexing device employing a linear scale.

DESCRIPTION OF PREFERRED EMBODIMENTS

Referring to FIGS. 1-3, the human reproduction indexing device 10 comprises a base member 11 and an index member 12 which are assembled together in interlocking engagement with the index member 12 being rotatable relative to the base member 11. The base member 11 has indicia representing the calendar dates for the days of a 31 day month disposed on its front surface 13. The numerical indicia are equally spaced around the peripheral edges of the front and back surfaces of the generally annular shaped base member 11.

The forward surface 16 of the indexing member 12 bears indexing indicia including an index 17 in the form of an arrow and an indicator 18 in the form of an arcuate segment 18 which indicates the calendar dates for seven days. One edge 19 of the indicator segment 18 is spaced from the index arrow 17 by a distance corresponding to a ten day separation so that the indicator segment 18 indicates the tenth through seventeenth days after the day indexed by the arrow 17. For example, as illustrated in FIG. 1, when the arrow 17 is indexed with calendar date 1, the indicator segment 18 indicates a seven day interval starting with calendar date 11 and ending with calendar date 18. Generally, ovulation should occur approximately fourteen days, and within 11 to 16 days, following the start of the menses, the date to which the index is set. This five day interval is indicated by the indicator segment 18 which has its midpoint indicating the time ovulation should occur, typically fourteen days after the onset of the menses.

Considering the indexing device 10 in more detail, as shown best in FIG. 3, the index member 12 has a generally cylindrical main body portion 21 having a peripheral flange 22 at one end which locates a shoulder 23. The shoulder 23 is spaced from the main body portion 21 defining an annular channel 25, which is also spaced from the peripheral edge deferring a stop surface 26 which is engaged by a shoulder 32 of the base member 11 when the two members are assembled together. The base member 11 and the index member 12 are preferably of an opaque plastic material and may be formed by injection molding, for example.

The base member 11 is a ring-shaped element having an offset annular channel 28 in which is received the shoulder 23 of the index member 12 when the two members are assembled together as shown in FIGS. 1 and 5. The rearward peripheral edge of member 11 is of a stepped configuration defining the shoulder 32 which engages the stop surface 26 of the index member. A peripheral lip 24 formed on the outer surface 27 of the shoulder 23 of the index member is received in a groove 30 formed on the opposing surface 31 of the base member 11. When the two pieces are assembled together, the lip 24 is "snapped" into the groove securing the index member to the base member. The shoulder 23 of the index member is resilient and notched as indicated at 33 to permit it to flex as the two pieces are pressed together.

Referring to FIG. 4, the front surface 13 of the base member 11 bears numerals 1 through 31, representing the calendar dates. The numerals and calibration marks 35 are equally spaced around the periphery of the surface 13. The index arrow 17 on the index member 12 extends radially from the center of the front surface 16 with its arrow head 17a located at the periphery of the surface 16 adjacent to the calibration marks 35. The width of the indicator segment 18 defined by angle a, is approximately 81°, so that, for a thirty-one day month, the segment 18 indicates the calendar dates for seven days of the month. The angular separation between the arrow head 17a and the edge 19 of the segment 19 is approximately 116°, providing a ten day separation between the date indexed by the arrow 17 and the first date indicated by segment 18. The calendar date indicia and the indexing indicia may be heat stamped on the base member and index member, respectively.

With reference to FIGS. 3 and 5, an annular-shaped bias spring 36 is located in the channel 25 formed in the index member and serves to urge the two members apart providing sufficient frictional engagment between the surfaces of the lip 24 and the groove 30 as to require deliberate rotation of the index member 12 relative to the base member 11, maintaining the index member 12 aligned with the calendar date to which it is set until the user resets the device.

A loop 38 is formed integrally with the base member 11 may be used to facilitate mounting of the indexing device 10.

In use, the indexing device 10 is set each month with the arrow 17 being aligned with the calendar date corresponding to the onset of the last menses. For example, assuming the last menstrual period started on the first day of the month, then the arrow 17 is set to calendar date 1 on the calendar scale.

To align the index member 12, the edges of the base member 11 are grasped with the fingers of one hand and the fingers of the other hand are used to grasp the edge of the index member 12, which has its edge serrated to aid in holding the index member with the fingers. The index member 11 is then rotated until the arrow 17 is pointing to calendar date 1. The red indicator segment 18 then indicates the calendar dates 11–18 which correspond to the seven days of that month in which the probability of conception is the greatest. Ovulation should occur on the 15th day of the month which is indicated near the middle of the set of calendar dates indicated by the indicator segment 18.

With the start of menstrual period at the end of the current menstrual cycle, the indexing device is reset so that the index 17 is aligned with the calendar date corresponding to the start of this period and a new set of dates is indicated by the indicator segment 18.

As indicated above, the front surface of the indexing device 10 is calibrated to a thirty-one day month. If desired, the back side of the device may be calibrated to a thirty day month and the back surface 19 of the index member 12 may bear an index 17′ and a corresponding indicator segment 18′ for indexing a seven day interval of the thirty day scale provided on the base. Also, separate scales may be provided on different portions of the same surface of the base member with suitable indexing indicia being provided on the index member. For the month of February, the device 10 may be set by subtracting two or three days from the index date, depending upon whether the thirty day or thirty-one day scale is being used.

Referring to FIG. 6, in accordance with another embodiment of the invention, a human reproduction indexing device 50 comprises a base member 51 and an index member 52, both of which are in the shape of flat discs of a suitable material, such as plastic, and which are held together at their centers by way of a suitable fastener, such as a rivet 53. The base member 51 carries calendar indicia representing calendar dates 1–31 and the indexing member 52 bears indexing indicia, including an index arrow 17 and an indicator segment 18 having the shape and orientation as the indexing shown in FIG. 4.

In the embodiment for the indexing device 50′ shown in FIG. 7, the diameter of the index member 52′ is approximately the same as the diameter of the base member 51 so that its peripheral edge overlies the calendar dates disposed on the upper surface of the base member. The indexing indicia of the index member are defined by cut out portions 57 and 58 in the index member which expose the calendar date indexed and the seven calendar dates for the corresponding seven day interval, respectively. In FIG. 8, there is shown an embodiment for the indexing device 60, wherein the sets of calendar dates representing the seven day intervals for each calendar date for a given month are disposed on the base member 61 and aligned radially with the corresponding calendar date on the base member 61. A single slot 63 provided in the index member 62 exposes the calendar date and its corresponding set of seven calendar dates. The indexing device 70 shown in FIG. 9 includes a base member 71, which has the calendar dates disposed in a linear scale. The index member 72 is in the form of an envelope which is open ended on each side with the base member 71 extending therethrough. It is apparent that an index member to those shown in FIGS. 6 and 7 can be employed for the linear scale indexing device shown in FIG. 9.

The manner of use of the devices shown in FIGS. 6–9 is apparent from the foregoing description for the embodiment shown in FIGS. 1–5.

Having thus disclosed in detail preferred embodiments fo the invention, persons skilled in the art will be able to modify certain of the structure which has been disclosed and to substitute equivalent elements for those which have been illustrated; and it is, therefore, intended that all such modifications and substitutions be covered as they are embraced within the spirit and scope of the appended claims.

I claim:

1. An indexing device comprising: a base member having calendar indicia representing the calendar dates for the days of one month interval disposed on at least one surface thereof, and an index member having indexing means including an indexing portion and an indicator portion, said index member being assembled together with said base member and being movable relative thereto to permit said indexing portion to be selectively aligned with said calendar indicia, said indicator portion being disposed in a predetermined relationship relative to said indexing portion whereby when said index member is set with said indexing portion aligned with a given one of the calendar indicia, said indicator portion is located to indicate a preselected group of the calendar dates.

2. An indexing device as set forth in claim 1 wherein said indicia representing the calendar dates includes a plurality of numerals each representing a different one of the days of the month, said numerals being disposed in a single circular track on said surface of said member, and wherein said indexing portion is in the shape of an arcuate segment of a predetermined number of angular degrees to thereby indicate a different preselected group of said numerals for different settings of said index member.

3. An indexing device as set forth in claim 2 wherein one edge of said indicator segment is located a preselected number of angular degrees from said indexing portion to thereby define an interval of a predetermined number of days between the calendar date indexed by the indexing portion and one of the calendar dates represented by the group of numbers indicated by said indicator segment.

4. An indexing device as set forth in claim 1 wherein said base member is circular in shape, said index member having a generally cylindrical main body portion extending through a central opening of said base member with a forward surface located adjacent to said indicia bearing surface of said base member and bearing said indexing means on a surface thereof, said index member having a flange portion adjacent to a rearward surface thereof and having means formed therewith for movably securing said index member to said base member.

5. A human reproduction indexing device for indicating the calendar dates for the days of a menstrual cycle on which the probability of conception is the greatest, said indexing device comprising: a base member having calendar indicia representing the calendar dates for the days of at least one month disposed in a single circular track on at least one surface thereof, and an index member having indexing means including an indexing portion and an indicator portion said index member being assembled together with said base member for rotatable movement relative thereto to permit said indexing portion to be selectively aligned with the indicia representing each of said calendar dates, and said indicator portion being disposed in a predetermined relationship relative to said indexing portion whereby when said index member is set to align said indexing means with the calendar day corresponding to the start of the mensus, said indicator portion is located to indicate the calendar dates for a set of calendar days on which the probability of conception is the greatest.

6. An indexing device as set forth in claim 5 wherein said index member overlies said calendar indicia on said base member and has at least one cut out portion defining said indexing means for selectively exposing to view each of said calendar dates and the corresponding set of calendar dates.

7. An indexing device as set forth in claim 5 wherein said calendar indicia are disposed on said base member in a linear scale.

8. An indexing device as set forth in claim 7 wherein said base member is a generally flat rectangular member, said index member being in the form of a generally rectangular envelope, open-ended at both ends with said base member extending therethrough.

9. An indexing device as set forth in claim 5 in which said base member and said index member are each of a flat generally circular configuration, and including means extending through the centers of said circular members securing said members together.

10. An indexing device as set forth in claim 5 wherein said index member has a circular surface disposed adjacent to said indicia bearing surface of said base member with indexing means being disposed on said surface of said index member and wherein said indexing portion defines an arcuate segment of a predetermined number of angular degrees to thereby indicate a preselected number of calendar dates for each setting of said index member.

11. An indexing device as set forth in claim 10 wherein one edge of said indicator segment is located a preselected number of angular degrees from said indexing means to thereby define an interval of a predetermined number of days between the calendar date indexed by said indexing means and one of the calendar dates indicated by the indicator segment.

12. An indexing device as set forth in claim 5 wherein said calendar indicia represent the calendar dates for a thirty-one day month, and wherein said base member includes further calendar indicia representing the calendar dates for a thirty day month disposed on a further surface thereof and said index member having further indexing means including an indexing portion and an indicator portion for selectively indexing each of said calendar dates of said further calendar indicia with the calendar dates of said further calendar indicia.

13. A human reproduction indexing device for indicating the calendar dates for days of a menstrual cycle on which the probability of conception is the greatest, said indexing device comprising: an annularly shaped base member having indicia representing calendar dates for days for at least a one month interval disposed on at least one surface thereof in a circular track, an indexing member movably secured to said base member for rotation relative thereto about an axis extending perpendicular to the center of said base member, said indexing member having indexing indicia disposed on a surface thereof, which is located adjacent to said indicia bearing surface of said base member, said indexing indicia including an index portion and an indicator portion defining an arcuate segment of preselected number of angular degrees to thereby indicate a preselected number of days, and one edge of said segment being located a preselected number of angular degrees away from said indexing means whereby when said indexing member is positioned with said indexing means aligned with the calendar day corresponding to the start of menses, said indicator means is located to indicate the calendar dates for the days of a menstrual cycle on which the probability of conception is the greatest.

14. An indexing device as set forth in claim 13 wherein said indicator segment indicates a different set of seven of said calendar dates for each of said calendar dates as indexed by said index portion.

15. An indexing device as set forth in claim 14 wherein said indicator segment indicates the calendar days for the tenth through seventeenth days following the calendar date indexed by said index portion.

16. A human reproduction indexing device for indicating the calendar dates for days of a menstrual cycle on which the probability of conception is the greatest, said indexing device comprising: an annularly shaped base member having indicia representing calendar days for at least a one month interval disposed on a surface thereof, said indicia including a plurality of numerals each representing a different day of the month disposed in an equal spaced relationship in a circle adjacent to the peripheral edge of said base member, and an index member having a generally cylindrical main body portion extending through a central aperture of said base member, receptor means formed integrally with one of said members and engaging means formed integrally with the other one of said members for engagement with said receptor means to secure said members together with said index member being rotatably relative to said base member about an axis extending perpendicular to the surface of said base member, spring means positioned in said receptor means and engageable with said engaging means to provide frictional engagement between said receptor and said engaging means, said index member having indexing means disposed on a surface of its central body portion and indicator means disposed in said surface, said indicator means defining an arcuate segment of a preselected number of angular degrees to thereby indicate a preselected number of calendar days, one edge of said segment being spaced from said indexing means by a preselected number of angular degrees whereby when said index member is positioned with said indexing means aligned with the calendar day corresponding to start the mensus, said indicator means is located to indicate the calendar dates for the days of a menstrual cycle on which the probability of conception is the greatest.

* * * * *